United States Patent [19]
Olsen et al.

[11] Patent Number: 5,916,769
[45] Date of Patent: Jun. 29, 1999

[54] POLYNUCLEOTIDES ENCODING EXTRA CELLULAR/EPIDERMAL GROWTH FACTOR HCABA58X POLYPEPIDES

[75] Inventors: Henrik S. Olsen, Gaithersburg; Steven M. Ruben, Olney, both of Md.

[73] Assignee: Human Genome Sciences, Inc., Rockville, Md.

[21] Appl. No.: 08/833,963

[22] Filed: Apr. 11, 1997

Related U.S. Application Data

[63] Continuation-in-part of application No. PCT/US96/05033, Apr. 10, 1996.

[51] Int. Cl.$^6$ .............................. C12N 1/21; C12N 15/12; C12N 15/63; C12N 5/00
[52] U.S. Cl. .................... 435/69.4; 435/69.1; 435/320.1; 435/325; 435/243; 536/23.1; 536/23.51
[58] Field of Search .................. 435/69.1, 69.4, 435/320.1, 325, 243; 536/23.1, 23.51

[56] References Cited

PUBLICATIONS

George et al. Macromolecular Sequencing & Synthesis Selected Methods & Applications, pp. 127–149, 1988.
Lecka–Czernik et al. Mol. Cell. Biol. 15(1):120–128, 1995.
Argraves, et al.,J. Cell Biol., III:3155–3164 (1990).
GenBank Accession No. F13193 (Mar. 5, 1995).
GenBank Accession No. T75316 (Mar. 3, 1995).
GenBank Accession No. H53813 (Sep. 20, 1995).
GenBank Accession No. R81318 (Jun. 12, 1995).
Bell, et al., Nucleic Acids Research, 143: 8427–8446 (1986).
Lecka–Czernik, et al., Mol. Cell. Biol., 15:120–128 (1995).
Salomon et al., Critical Rev. Oncol. Hematol. 19:183–232 (1995).
Bell et al., 1986, *Nucleic Acids Research*, 143:8427–8446.
Lecka–Czernik et al., 1995, *Mol. Cell Biol.*, 15:120–128.
Salomon et al., 1995, *Critical Rev. Oncol. Hematol.* 19:183–232.

*Primary Examiner*—John Ulm
*Assistant Examiner*—Christine Saoud
*Attorney, Agent, or Firm*—A. Anders Brookes; Joseph J. Kenny

[57] ABSTRACT

The present invention discloses a novel cDNA isolated from human osteoclastoma tissue which encodes a novel polypeptide identified herein as Extracellular/Epidermal Growth Factor HCABA58X owing in part to the presence in its amino acid sequence of epidermal growth factor (EGF) domains characteristic of the EGF family of polypeptides. Also provided are procedures for producing such polypeptides by recombinant techniques and therapeutic uses of the polypeptides. Also disclosed are antagonists against such polypeptides and their uses. Also disclosed are diagnostic assays for detecting altered levels of the polypeptides of the present invention and mutations in the nucleic acid sequences which encode such polypeptides.

26 Claims, 7 Drawing Sheets

```
  1  GGAATTCGGCACGAGGCGTCCAGGGAGCTGTGCGCCCGTCCGTCTGCCCGCAGGCA
     ------+---------+---------+---------+---------+---------+   60

61  TTGCCCGAGCCAGCCGAGCCGCCAGAGCCGCGGGGTGTCGCGGGCCCAACCC
     ------+---------+---------+---------+---------+---------+  120

121  CAGGATGCTCCCCTGCGCCTCCTGCCCTGGGTCTCTCTACTGCTCTGGGCGCTGCTACT
     ------+---------+---------+---------+---------+---------+  180
         MetLeuProCysAlaSerCysLeuProGlySerLeuLeuLeuTrpAlaLeuLeuLe
          M  L  P  C  A  S  C  L  P  G  S  L  L  L  W  A  L  L  L

181  GTTGCTCTTGGATCAGCTTCTCCTCAGGATTCTGAAGAGCCCGACAGCTACACGGAATG
     ------+---------+---------+---------+---------+---------+  240
     uLeuLeuLeuGlySerAlaSerProGlnAspSerGluGluProAspSerTyrThrGluCy
      L  L  L  G  S  A  S  P  Q  D  S  E  E  P  D  S  Y  T  E  C

241  CACAGATGGCTATGAGTGGGACCCAGACAGCCAGCACTGCCGGGATGTCAACGAGTGTCT
     ------+---------+---------+---------+---------+---------+  300
     sThrAspGlyTyrGluTrpAspProAspSerGlnHisCysArgAspValAsnGluCysLe
      T  D  G  Y  E  W  D  P  D  S  Q  H  C  R  D  V  N  E  C  L

301  GACCATCCCTGAGGCCTGCAAGGGGGAAATGAAGTGCATCAACCACTACGGGGCTACTT
     ------+---------+---------+---------+---------+---------+  360
     uThrIleProGluAlaCysLysGlyGluMetLysCysIleAsnHisTyrGlyGlyTyrLe
      T  I  P  E  A  C  K  G  E  M  K  C  I  N  H  Y  G  G  Y  L
```

FIG. 1A

MATCH WITH FIG. 1B

FIG. 1B

MATCH WITH FIG. 1A

```
      GTGCCTGCCCCGCTCCGCTCCGCTGCCGTCATCAACGACCTACACGGGCGAGGGACCCCCGCCACC
361   ---------+---------+---------+---------+---------+---------+  420
      uCysLeuProArgSerAlaAlaValIleAsnAspLeuHisGlyGluGlyProProPr
        C  L  P  R  S  A  A  V  I  N  D  L  H  G  E  G  P  P  P  P

AGTGCCTCCCGCTCAACACCCCTGCCCACCAGGCTATGAGCCCGACGATCAGGA
421   ---------+---------+---------+---------+---------+---------+  480
      oValProProAlaGlnHisProAsnProCysProProGlyTyrGluProAspAspGlnAs
        V  P  P  A  Q  H  P  N  P  C  P  P  G  Y  E  P  D  D  Q  D

CAGCTGTGTGGATGTGGACGAGTGTGCCCAGGCCCTGCACGACTGTCGCCCCAGCCAGGA
481   ---------+---------+---------+---------+---------+---------+  540
      pSerCysValAspValAspGluCysAlaGlnAlaLeuHisAspCysArgProSerGlnAs
        S  C  V  D  V  D  E  C  A  Q  A  L  H  D  C  R  P  S  Q  D

CTGCCATAACTTGCCTGGCTCCTATCAGTGCACCTGCCCTGATGGTTACCGCAAGATCGG
541   ---------+---------+---------+---------+---------+---------+  600
      pCysHisAsnLeuProGlySerTyrGlnCysThrCysProAspGlyTyrArgLysIleGl
        C  H  N  L  P  G  S  Y  Q  C  T  C  P  D  G  Y  R  K  I  G

GCCCGAGTGTGTGGACATAGAGTGCCGCTACCGCTACTGCCAGCACCGCTGCGTGAA
601   ---------+---------+---------+---------+---------+---------+  660
      yProGluCysValAspIleAspGluCysArgTyrArgTyrCysGlnHisArgCysValAs
        P  E  C  V  D  I  D  E  C  R  Y  R  Y  C  Q  H  R  C  V  N
```

MATCH WITH FIG. 1C

FIG. 1C

MATCH WITH FIG. 1D

```
661  CCTGCCTGGCTCCTTCCGCTGCCAGTGCGAGCCGGGCTTCCAGCTGGGGCCTAACAACCG
     ----+----+----+----+----+----+----+----+----+----+----+----+  720
     nLeuProGlySerPheArgCysGlnCysGluProGlyPheGlnLeuGlyProAsnAsnAr
      L  P  G  S  F  R  C  Q  C  E  P  G  F  Q  L  G  P  N  N  R

721  CTCCTGTGTTGATGTGAACGAGTGTGACATGGGGGCCCCATGCGAGCAGCGCTGCTTCAA
     ----+----+----+----+----+----+----+----+----+----+----+----+  780
     gSerCysValAspValAsnGluCysAspMetGlyAlaProCysGluGlnArgCysPheAs
      S  C  V  D  V  N  E  C  D  M  G  A  P  C  E  Q  R  C  F  N

781  CTCCTATGGGACCTTCCTGTGTCGCTGCCACCAGGGCTATGAGCTGCATCGGGATGGCTT
     ----+----+----+----+----+----+----+----+----+----+----+----+  840
     nSerTyrGlyThrPheLeuCysArgCysHisGlnGlyTyrGluLeuHisArgAspGlyPh
      S  Y  G  T  F  L  C  R  C  H  Q  G  Y  E  L  H  R  D  G  F

841  CTCCTGCAGTGATATTGATGAGTGTAGCTACTCCAGCTCCTCTGTCAGTACCGCTGCGT
     ----+----+----+----+----+----+----+----+----+----+----+----+  900
     eSerCysSerAspIleAspGluCysSerTyrSerSerTyrLeuCysGlnTyrArgCysVa
      S  C  S  D  I  D  E  C  S  Y  S  S  Y  L  C  Q  Y  R  C  V

901  CAACGAGCCAGGCCGTTTCTCCTGCCACTGCCCACAGGGTTACCAGTGCTGGCCACACG
     ----+----+----+----+----+----+----+----+----+----+----+----+  960
     lAsnGluProGlyArgPheSerCysHisCysProGlnGlyTyrGlnLeuLeuAlaThrAr
      N  E  P  G  R  F  S  C  H  C  P  Q  G  Y  Q  L  L  A  T  R
```

MATCH WITH FIG. 1C

```
      CCTCTGCCAAGACATTGATGAGTGTGAGTCTGGTGCGCACCAGTGCTCCGAGGCCCAAAC
961   ------+---------+---------+---------+---------+---------+ 1020
      gLeuCysGlnAspIleAspGluCysGluSerGlyAlaHisGlnCysSerGluAlaGlnTh
       L  Q  D  I  D  E  C  E  S  G  A  H  Q  C  S  E  A  Q  T

CTGTGTCAACTTCCATGGGGCTACCGCTGCGTGGACACCAACCGTTGCGTGGAGCCCTA
1021  ------+---------+---------+---------+---------+---------+ 1080
      rCysValAsnPheHisGlyGlyTyrArgCysValAspThrAsnArgCysValGluProTy
       C  V  N  F  H  G  G  Y  R  C  V  D  T  N  R  C  V  E  P  Y

CATCCAGGTCTCTGAGAACCGCTGTCTCTGCCCGGCCTCCAACCCTCTATGTCGAGAGCA
1081  ------+---------+---------+---------+---------+---------+ 1140
      rIleGlnValSerGluAsnArgCysLeuCysProAlaSerAsnProLeuCysArgGluGl
       I  Q  V  S  E  N  R  C  L  C  P  A  S  N  P  L  C  R  E  Q

GCCTTCATCCATTGTGCACCGCTACAATGACCATCACCTCGGAGCGGAGCGTGCCCGCTGA
1141  ------+---------+---------+---------+---------+---------+ 1200
      nProSerIleValHisArgTyrMetThrIleThrSerGluArgSerValProAlaAs
       P  S  I  V  H  R  Y  M  T  I  T  S  E  R  S  V  P  A  D

CGTGTTCCAGATCCAGGCGACCTCCGTCTACCCCGGTGCCTACAATGCCTTTCAGATCCG
1201  ------+---------+---------+---------+---------+---------+ 1260
      pValPheGlnIleGlnAlaThrSerValTyrProGlyAlaTyrAsnAlaPheGlnIleAr
       V  F  Q  I  Q  A  T  S  V  Y  P  G  A  Y  N  A  F  Q  I  R
```

FIG. 1D

MATCH WITH FIG. 1E

MATCH WITH FIG. 1D

```
1261  TGCTGGAAACTCGCAGGGGACTTTTACATTAGGCAAATCAACAACGTCAGGCGCCATGCT
      ------+---------+---------+---------+---------+---------+  1320
      gAlaGlyAsnSerGlnGlyAspPheTyrIleArgGlnIleAsnAsnValSerAlaMetLe
        A  G  N  S  Q  G  D  F  Y  I  R  Q  I  N  N  V  S  A  M  L

1321  GGTCCTCGCCCGGCCCGGTGACGGGCCCCCGGGAGTACGTGCTGGACCTGGAGATGGTCAC
      ------+---------+---------+---------+---------+---------+  1380
      uValLeuAlaArgProValThrGlyProArgGluTyrValLeuAspLeuGluMetValTh
        V  L  A  R  P  V  T  G  P  R  E  Y  V  L  D  L  E  M  V  T

1381  CATGAATTCCCTCATGAGCTACCGGGCCAGCTCTGTACTGAGGCTCACCGTCTTTGTAGG
      ------+---------+---------+---------+---------+---------+  1440
      rMetAsnSerLeuMetSerTyrArgAlaSerSerValLeuArgLeuThrValPheValGl
        M  N  S  L  M  S  Y  R  A  S  S  V  L  R  L  T  V  F  V  G

1441  GGCCTACACCTTCTGAGGAGCAGGAGGAGCCACCCTCCCCTGCAGCTACCCTAGCTGAGG
      ------+---------+---------+---------+---------+---------+  1500
      yAlaTyrThrPhe
        A  Y  T  F

1501  AGCCTGTTGTGAGGGGCAGAATGAG
      ------+---------+-----  1525
```

FIG. 1E

```
           10         20         30         40         50
MATSGVLPGGGFVASAAAVAGPEMQTGRNNFVIRRNPADPQRIPSNPS-HRIQCAAG
                            |::  ||:  ::  |::  |::  :|::|
            RDVNECLTIPEACKGEMKCINHYGGYLCLPRSAAVINDLHGEGPPPVPPAQHPNPCPPG 60         70         80         90        100        110
YEQSEHNVCQDIDECTAGTHNCRADQVCINLRGSFACQCPPGYQKRGEQCVDIDECTIPP
|||:::|  :|:||||  |||:  ::| ::|  | |||:||||:|||:||||||||  :
YEPDDQDSCVDVDECAQALHDCRPSQDCHNLPGSYQCTCPDGYRKIGPECVDIDECRY-R 120        130        140        150        160        170
YCHQRCVNTPGSFYCQCSPGFQLAANNYTCVDINECDASNQCAQQCYNILGSFICQCNQG
|||:|||| |||| ||| ||||| |:::|||||||| | :|||  ||| : | |||:||
YCQNRCVNLPGSFRCQCEPGFQLGPNNRSCVDVNECDMGAPCEQRCFNSYGTFLCRCHQG 180        190        200        210        220        230
YELSSDRLNCEDIDECRTSSYLCQYQCVNEPGKFSCMCPQGYQVVRSRTCQDINECET-T
|||  |:| ||:||||| |||| | | |||| |||:|||||| : ::|||||||| | |
YELHRDGFSCSDIDECSYSSYLCQYRCVNEPGRFSCHCPQGYQLLATRLCQDIDECESGA
```

FIG. 2A

MATCH WITH FIG. 2B

```
240                250                260                270                280                290
NECREDEMCWNYHGGFRCYPRNPCQDPYILTPENRCVCPVSNAMCRELPQSIVYKYMSIR
::|::|||:::|:|:|||::||::|::||:::||:|||:|::|||||::||:|:|
HQCSEAQTCVNFHGGYRCVDTNRCVEPYIQVSENRCLCPASNPLCREQPSSIVHRYMTIT 300                310                320                330                340                350
SDRSVVPSDIFQIQATTIYANTINTFRIKSGNENGEFYLRQTSPVSAMLVLVKSLSGPREH
|:|||:|:|||||:||:|:|||::||:|::|:|::::|||:||:|||:||||||||:|||
SERSVPADVFQIQATSVYPGAYNAFQIRAGNSQGDFYIRQINNVSAMLVLARPVTGPREY
     4

360                370                380
IVDLEMLTVSSIGTFRTSSVLRLTIIVGPFSF
::|||||:|::|::|:|||||||||:::::|
VLDLEMVTMNSLMSYRASSVLRLTVFVGAYTF
```

FIG. 2B

POLYNUCLEOTIDES ENCODING EXTRA CELLULAR/EPIDERMAL GROWTH FACTOR HCABA58X POLYPEPIDES

This application is a continuation-in-part application of, and claims benefit of 35 U.S.C. §120 to, copending U.S. patent application Ser. No. PCT/US96/05033, filed Apr. 10, 1996.

This invention relates to newly identified polynucleotides, polypeptides encoded by such polynucleotides, the use of such polynucleotides and polypeptides, as well as the production of such polynucleotides and polypeptides. The polypeptide of the present invention has been putatively identified as a human extracellular protein-like/Epidermal Growth Factor-like protein, hereafter referred to as "HCABA58X". The invention also relates to inhibiting the action of such polypeptides.

Cellular growth and differentiation appear to be initiated, promoted, maintained and regulated by a multiplicity of stimulatory, inhibitory and synergistic factors and hormones. The alteration and/or breakdown of the cellular homeostasis mechanism seems to be a fundamental cause of growth related diseases, including neoplasia. Growth modulatory factors are implicated in a wide variety of pathological and physiological processes including signal transduction, cell communication, growth and development, embryogenesis, immune response, hematopoiesis cell survival and differentiation, inflammation, tissue repair and remodeling, atherosclerosis and cancer. Epidermal growth factor (EGF), transforming growth factor alpha TGFα), betacellulin, amphiregulin, and vaccinia growth factor among other factors are growth and differentiation modulatory proteins produced by a variety of cell types either under normal physiological conditions or in response to exogenous stimuli and are members of the EGF family.

These peptide growth factors influence epithelial and epidermal cells through autocrine and paracrine mechanisms. They also play important roles in normal wound healing in tissues such as skin, cornea and gastrointestinal tract and all share substantial amino acid sequence homology including the conserved placement of three intra-chain disulfide bonds. In addition, all the factors of this family bind to a 170,000 molecular weight transmembrane glycoprotein receptor and activate the tyrosine kinase activity in the receptor's cytoplasmic domain (Buhrow, S. A. et al., *J. Bio.Chem.*, 258:7824–7826 (1983)).

The receptors are expressed by many types of cells including skin keratinocytes, fibroblasts, vascular endothelial cells, and epithelial cells of the gastrointestinal tract (GI) tract. These peptide growth factors are synthesized by several cells involved in wound healing including platelets, keratinocytes, and activated macrophages. These growth factors have also been implicated in both the stimulation of growth and differentiation of certain cells, for example, neoplasia, and the inhibition of other types of cells.

Betacellulin is a 32-kilodalton glycoprotein that appears to be processed from a larger transmembrane precursor by proteolytic cleavage. The carboxyl-terminal domain of betacellulin has 50% sequence similarity with that of rat transforming growth factor α. Betacellulin is a potent mitogen for retinal pigment epithelial cells and vascular smooth muscle cells.

Amphiregulin is a bifunctional cell growth regulatory factor which exhibits potent inhibitory activity on DNA synthesis in neoplastic cells, yet promotes the growth of certain normal cells. A wide variety of uses for amphiregulin have been assigned including the treatment of wounds and cancers. For example, amphiregulin has potent antiproliferative effects in vitro on several human cancer cell lines of epithelial origin. Amphiregulin also induces the proliferation of human foreskin fibroblasts as shown in U.S. patent application Ser. No. 5,115,096.

TGFα has pleiotropic biological effects. The production of certain members of TGFα is synthesized by a number of oncogenically transformed fibroblasts (Ciardiello et al., *J. Cell. Biochem.*, 42:45–57 (1990)), as well as by a variety of tumors, including renal, breast and squamous carcinomas, melanomas and glioblastomas (Derynck, R. et al., *Cancer Res.*, 47:707–712 (1987)). There is direct evidence that TGFα expression can be a contributing factor in the conversion of a normal cell to its tumorigenic counterpart by analyzing transgenic mice in which tumor cells express high levels of TGFα. TGFα transgenic animals display a variety of neoplastic lesions, depending on the strain of mouse and the choice of promotor regulating TGFα expression (Sandgren, et al., *Cell,* 61:1121–1135 (1990)).

TGFα also plays a role in normal embryonic development and adult physiology (Derynck, R. *Adv. Cancer Res.*, 58:27–5 (1992)). TGFα has been expressed in many tissues including skin, brain, gastrointestinal mucosa and activating macrophages. Accordingly, TGFα is an important factor in controlling growth of epithelial cells and has a role in wound healing. TGFα has also been found to be angiogenic (Schreiber, et al., *Science,* 232:1250–1253 (1986)).

The polypeptide of the present invention has been putatively identified as an Extracellular/Epidermal Growth Factor. This identification has been made as a result of amino acid sequence homology to human Extracellular protein which is a secreted protein with EGF-like domains that is abundant in heart tissue and is disclosed in Lecka-Czernik et al., Molecular and Cellular Biology, 15(1):120–128 (1995).

In accordance with one aspect of the present invention, there are provided novel mature polypeptides, as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides of the present invention, including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the human cDNA contained in ATCC Deposit No. 97376.

In accordance with yet a further aspect of the present invention, there are provided processes for producing such polypeptide by recombinant techniques comprising culturing recombinant prokaryotic and/or eukaryotic host cells, containing a nucleic acid sequence encoding a polypeptide of the present invention.

In accordance with yet a further aspect of the present invention, there are provided processes for utilizing such polypeptides, or polynucleotides encoding such polypeptides for therapeutic purposes, for example, to regulate vascular smooth muscle cell proliferation, to treat Marfan syndrome, to stimulate wound healing, to restore normal neurological functioning after trauma or AIDS dementia, to treat ocular disorders, to treat kidney and liver disorders, to promote hair follicular development, to stimulate growth and differentiation of various epidermal and epithelial cells in vivo and in vitro and for the treatment of burns, ulcers and corneal incisions, to stimulate embryogenesis.

In accordance with yet a further aspect of the present invention, there is also provided nucleic acid probes comprising nucleic acid molecules of sufficient length to specifically hybridize to nucleic acid sequences of the present invention.

In accordance with yet a further aspect of the present invention, there are provided antibodies against such polypeptides.

In accordance with yet a further aspect of the present invention, there are provided agonists to the polypeptide of the present invention.

In accordance with yet another aspect of the present invention, there are provided antagonists to such polypeptides, which may be used to inhibit the action of such polypeptides, for example, in the treatment of corneal inflammation, neoplasia, for example, tumors and cancers, for psoriasis and diabetes.

In accordance with still another aspect of the present invention, there are provided diagnostic assays for detecting diseases related to overexpression of the polypeptide of the present invention and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–1E depicts the cDNA sequence and corresponding deduced amino acid sequence of HCABA58X. Both the standard one letter and three letter abbreviations for amino acids are used.

FIGS. 2A and 2B is an illustration of comparative amino acid sequence homology between the polypeptide of the present invention (lower line) and human extracellular protein (upper line) (SEQ ID NO:9).

In accordance with an aspect of the present invention, there is provided an isolated nucleic acid (polynucleotide) which encodes for the mature polypeptide having the deduced amino acid sequence of FIGS. 1A–1E (SEQ ID NO:2).

A polynucleotide encoding a polypeptide of the present invention may be obtained from human brain and early stage brain tissue. The polynucleotide of this invention was discovered in a human osteoclastoma cDNA library. It has homology to the characteristic EGF domains. It contains an open reading frame encoding a polypeptide of 443 amino acids with a putative leader sequence of 24 amino acids. HCABA58X exhibits the highest degree of homology at the amino acid level to human extracellular protein with 51% identity and 30% similarity over a 387 amino acid stretch. Northern blot analysis of this protein shows high levels of expression in heart and kidney tissue with the transcript being approximately 2 kb.

In accordance with another aspect of the present invention there are provided isolated polynucleotides encoding a mature polypeptide expressed by the DNA contained in ATCC Deposit No. 97376 deposited with the American Type Culture Collection, 10801 University Boulevard, Manassas, Va. 20110-2209, USA, on Dec. 8, 1995 deposited as "PF258". The deposited material is a pbluescript SK (+) plasmid (Stratagene, La Jolla, Calif.) that contains the full-length HCABA58X cDNA.

The deposit(s) have been made under the terms of the Budapest Treaty on the International Recognition of the Deposit of Micro-organisms for purposes of Patent Procedure. The strain will be irrevocably and without restriction or condition released to the public upon the issuance of a patent. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are controlling in the event of any conflict with any description of sequences herein. A license may be required to make, use or sell the deposited materials, and no such license is hereby granted. References to "polynucleotides" throughout this specification includes the DNA of the deposit referred to above.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1E (SEQ ID NO:1) or may be a different coding sequence which coding sequence, as a result of the redundancy or degeneracy of the genetic code, encodes the same mature polypeptide as the DNA of FIGS. 1A–1E (SEQ ID NO:1).

The polynucleotide which encodes for the mature polypeptide of FIGS. 1A–1E (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1E (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1E (SEQ ID NO:2) as well as variants of such polynucleotides which variants encode for a fragment, derivative or analog of the polypeptide of FIGS. 1A–1E (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1E (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length HCABA58X gene may be used as a hybridization probe for a cDNA library to isolate the full length gene and to isolate other genes which have a high sequence similarity to the gene or similar biological activity. Probes of this type have at least 15 bases, preferably at least 30 bases and may contain, for example, 50 or more bases. The probe may also be used to identify a cDNA clone corresponding to a full length transcript and a genomic clone or clones that contain the complete HCABA58X gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1E (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 and polynucleotides complementary thereto as well as portions thereof, which portions have at least 15 consecutive bases, preferably at least 30 consecutive bases and most preferably at least 50 consecutive bases and to polypeptides encoded by such polynucleotides.

The present invention further relates to a polypeptide which has the deduced amino acid sequence of FIGS. 1A–1E (SEQ ID NO:2), as well as fragments, analogs and derivatives of such polypeptide.

The terms "fragment," "derivative" and "analog" when referring to the polypeptide of FIGS. 1A–1E (SEQ ID NO:2), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1E (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptides synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics for human disease.

The polypeptide of the present invention may be employed to to regulate vascular smooth muscle cell proliferation.

The polypeptide of the present invention may also be employed for characterization of receptors. The EGF family receptors currently includes four EGF receptors, denoted as EGFR1, EGFR2, EGFR3 and EGFR4. The EGFR2 receptor may also be referred to as ERB-2 and this molecule is useful for a variety of diagnostic and therapeutic indications (Prigent, S. A., and Lemoine, N. R., *Prog Growth Factor Res.*, 4:1–24 (1992)). The HCABA58X polypeptide is likely a ligand for one or more of these receptors as well as for an un-identified new EGF-type receptor. Use of the HCABA58X can assist with the identification, characterization and cloning of such receptors. For example, the EGF receptor gene represents the cellular homolog of the v-erb-B oncogene of avian erythroblastosis virus. Over expression of the EGF-receptor or deletion of kinase regulatory segments of the protein can bring about tumorigenic transformation of cells (Manjusri, D. et al., *Human Cytokines*, 364 and 381 (1991)).

The polypeptides of the present invention may also be employed for restoration or enhancement of neurological functions diminished as a result of trauma or other damaging pathologies (such as AIDS dementia, senile dementia, etc). TGFα and its homologs have been found to be the most abundant ligand for the EGF/TGFα receptor in most parts of the brain (Kaser, et al., Mol Brain Res: 16:316–322, (1992)). HCABA58X or soluble form thereof may also be employed to treat ocular disorders, for example, corneal inflammation. A variety of experiments have implicated members of the TGFα gene family in such pathologies. A recent paper summarizes some of the data related to the role these growth factors play in eye disease (Mann, et al, Cell, 73:249–261 (1993)). Recent experiments have shown that a number of mice lacking the TGFα gene displayed corneal inflammation due to an infiltration of leukocytes and other cells to the substantia propria of the eyes.

In addition, the specificity of certain growth factors for their target cells can be exploited as a mechanism to destroy the target cell. For example, HCABA58X or soluble forms thereof can be coupled, by a wide variety of methods known in the art, to toxic molecules: for example, a radiopharmaceutical which inactivate target cells. These growth factor-toxin fusions kill the target cell (and in certain cases neighboring cells by a variety of "bystander" effects). A recent example of such toxin-fusion genes is published by Mesri, et al., J. Biol. Chem. 268:4853–62 (1993). HCABA58X and related molecules may also be encapsulated in liposomes and may be conjugated to antibodies which recognize and bind to tumor or cell specific antigens, thereby provided a means for "targeting" cells.

The HCABA58X polypeptide may also be employed to treat certain kidney disorders, since it has been found that there has been expression of these growth factors in the kidney. Thus, these factors may be necessary for the proper physiological maintenance of this organ. Treatments may also be related to liver regeneration or liver dysfunction.

A significant treatment involving HCABA58X relates to wound healing. The compositions of the present invention may be employed for treating a wide variety of wounds including substantially all cutaneous wounds, corneal wounds, and injuries to the epithelial-lined hollow organs of the body. Wounds suitable for treatment include those resulting from trauma such as burns, abrasions and cuts, as well as from surgical procedures such as surgical incisions and skin grafting. Other conditions suitable for treatment with the polypeptide of the present invention include chronic conditions, such as chronic ulcers, diabetic ulcers, other non-healing (trophic) conditions, to treat Marfan syndrome, to promote hair follicular development, to stimulate growth and differentiation of various epidermal and epithelial cells in vivo and in vitro and to stimulate embryogenesis.

HCABA58X or soluble fragment thereof may be incorporated in physiologically-acceptable carriers for application to the affected area. The nature of the carriers may vary widely and will depend on the intended location of application. For application to the skin, a cream or ointment base is usually preferred; suitable bases include lanolin, Silvadene (Marion) (particularly for the treatment of burns), Aquaphor (Duke Laboratories, South Norwalk, Conn.), and the like. If desired, it will be possible to incorporate HCABA58X containing compositions in bandages and other wound dressings to provide for continuous exposure of the wound to the peptide. Aerosol applications may also find use.

The concentration of HCABA58X in the treatment composition is not critical but should be enough to induce epithelial cell proliferation. The compositions may be applied topically to the affected area, typically as eye drops to the eye or as creams, ointments or lotions to the skin. In the case of the eyes, frequent treatment is desirable, usually being applied at intervals of 4 hours or less. On the skin, it is desirable to continually maintain the treatment composition on the affected area during the healing, with applications of the treatment composition from two to four times a day or more frequently.

The amount employed of the subject polypeptide will vary with the manner of administration, the employment of other active compounds, and the like, generally being in the range of about 1 µg to 100 µg. The subject polypeptide may be employed with a physiologically acceptable carrier, such as saline, phosphate-buffered saline, or the like. The amount of compound employed will be determined empirically, based on the response of cells in vitro and response of experimental animals to the subject polypeptides or formulations containing the subject polypeptides.

The HCABA58X or soluble fragment thereof may be employed in the modulation of angiogenesis, bone resorption, immune response, and synaptic and neuronal effector functions. HCABA58X may also be used in the modulation of the arachidonic acid cascade.

Applications are also related to alopecia, hair loss and to other skin conditions which affect hair follicular development. Several lines of evidence implicate the involvement of growth factors in such conditions. As described above, "knockout" mice engineered to contain a null mutation in the TGFα gene display abnormalities related to quantitative and qualitative hair synthesis. In addition, mapping studies in mice have shown that some mutations affecting hair growth map to the TGFα gene locus (Mann et al, Cell, 73:249–261(1993)). Topical or systemic applications of HCABA58X or derivatives thereof may be employed to treat some forms of alopecia and hair loss and these claims fall within the scope of this invention.

Certain disease pathologies may be partially or completely ameliorated by the systemic clinical administration of the HCABA58X growth factor. This administration can be in the form of gene therapy (see below); or through the administration of peptides or proteins synthesized from recombinant constructs of HCABA58X DNA or from peptide chemical synthesis (Woo, et al., Protein Engineering 3:29–37 (1989).

This invention provides a method for identification of HCABA58X receptors. The gene encoding a receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to HCABA58X, and a cDNA library created from this RNA is divided into pools and used to transfect COS cells or other cells that are not responsive to HCABA58X. Transfected cells which are grown on glass slides are exposed to labeled HCABA58X, which can be labeled by a variety of means including iodination or inclusion of a recognition site for a site-specific protein kinase. Following fixation and incubation, the slides are subjected to autoradiographic analysis. Positive pools are identified and subpools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention also provides a method of screening compounds to identify antagonist compounds to the polypeptide of the present invention. As an example, a mammalian cell or membrane preparation expressing an HCABA58X receptor is incubated with HCABA58X and a potential antagonist compound and the ability of the compound to inhibit a second signal from the receptor is measured to determine if it is an effective antagonist. Such second messenger systems include but are not limited to, cAMP guanylate cyclase, ion channels or phosphoinositide hydrolysis.

Another assay for identifying potential antagonists specific to the receptors to the polypeptide of the present invention is a competition assay which comprises isolating plasma membranes which over-express a receptor to the polypeptide of the present invention, for example, human A431 carcinoma cells. Serially diluted test sample in a medium (volume is approximately 10 microliters) containing 10 nM $^{125}$I-HCABA58X is added to five micrograms of the plasma membrane in the presence of the potential antagonist compound and incubated for 4 hours at 4° C. The reaction mixtures are diluted and immediately passed through a millipore filter. The filters are then rapidly washed and the bound radioactivity is measured in a gamma counter. The amount of bound HCABA58X is then measured. A control assay is also performed in the absence of the compound to determine if the antagonists reduce the amount of bound HCABA58X.

Potential antagonist compounds include an antibody, or in some cases, an oligopeptide, which binds to the polypeptide. Alternatively, a potential antagonist may be a closely related protein which binds to the receptor which is an inactive forms of the polypeptide and thereby prevent the action of the polypeptide of the present invention.

Another antagonist compound is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptide of the present invention. The antisense RNA oligonucleotide hybridizes to the mRNA in vivo and blocks translation of the mRNA molecule into the polypeptide of the present invention (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide of the present invention.

Antagonist compounds include a small molecule which binds to the polypeptide of the present invention and blocks its action at the receptor such that normal biological activity is prevented. The small molecules may also bind the receptor to the polypeptide to prevent binding. Examples of small molecules include but are not limited to small peptides or peptide-like molecules.

The antagonists may be employed to treat neoplasia, for example, cancers and tumors. It is known that inhibition of secretion or production of members of the EGF family by tumor cells in mice causes regression of tumors, since these proteins stimulate induction of DNA synthesis in all cells including neoplastic cells.

The antagonists to the polypeptides of the present invention may also be used therapeutically for the treatment of certain skin disorders, for example, psoriasis. Elevated levels of expression of members of this family of growth factors in skin biopsies taken from diseases such as psoriatic lesions have been found to be elevated (Cook, et al., Cancer Research, 52:3224–3227 (1992)). The antagonists may be employed in a composition with a pharmaceutically acceptable carrier, e.g., as hereinafter described.

The antagonists to the polypeptides of the present invention may also be used therapeutically for the treatment of diabetes.

The polypeptides of the present invention or antagonist compounds may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or compounds of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 ηg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The polypeptides, and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene of the present invention will allow a diagnosis of a disease or a susceptibility to a disease which results from underexpression of the polypeptide of the present invention, for example, improper wound healing, improper neurological functioning, ocular disorders, kidney and liver disorders, hair follicular development, angiogenesis and embryogenesis.

Individuals carrying mutations in the human gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding a polypeptide of the present invention can be used to identify and analyze mutations thereof. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to diagnostic assays for detecting altered levels of the polypeptide of the present invention in various tissues since an over-expression of the proteins compared to normal control tissue samples can detect the presence of certain disease conditions such as neoplasia, skin disorders, ocular disorders and inflammation. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to an antigen of the polypeptide of the present invention, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to polypeptides of the present invention. Unattached reporter antibody is then washed out. Peroxidase substrates are then added to the dish and the amount of color developed in a given time period is a measurement of the amount of protein present in a given volume of patient sample when compared against a standard curve.

A competition assay may also be employed to determine levels of the polypeptide of the present invention in a sample derived from the hosts. Such an assay comprises isolating plasma membranes which over-express the receptor for the polypeptide of the present invention. A test sample containing the polypeptides of the present invention which have been labeled, are then added to the plasma membranes and then incubated for a set period of time. Also added to the reaction mixture is a sample derived from a host which is suspected of containing the polypeptide of the present invention. The reaction mixtures are then passed through a filter which is rapidly washed and the bound radioactivity is then measured to determine the amount of competition for the receptors and therefore the amount of the polypeptides of the present invention in the sample.

Antibodies specific to HCABA58X may be used for cancer diagnosis and therapy, since many types of cancer cells up-regulate various members of the TGFα family during the process of neoplasia or hyperplasia. These antibodies bind to and inactivate HCABA58X. Monoclonal antibodies against HCABA58X (and/or its family members) may be used for both the diagnosis and therapy of certain disorders including (but not limited to) hyperplastic and neoplastic growth abnormalities. Upregulation of growth factor expression by neoplastic tissues forms the basis for a variety of serum assays which detect increases in growth factor in the blood of affected patients. These assays are typically applied not only in diagnostic settings, but are applied in prognostic settings as well (to detect the presence of occult tumor cells following surgery, chemotherapy, etc).

In addition, malignant cells expressing the HCABA58X receptor may be detected by using labeled HCABA58X in a receptor binding assay, or by the use of antibodies to the HCABA58X receptor itself. Cells may be distinguished in accordance with the presence and density of receptors for HCABA58X, thereby providing a means for predicting the susceptibility of such cells to the biological activities of HCABA58X.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of HCABA58X

The DNA sequence encoding HCABA58X, ATCC # 97376, is initially amplified using PCR oligonucleotide primers corresponding to the 5' sequences of the processed protein and the sequences 3' of the HCABA58X gene. The 5' oligonucleotide primer has the sequence 5' GATCGCATGCTCCCCTGCGCCTCCTG 3' (SEQ ID NO:3) contains a SphI restriction enzyme site followed by 17 nucleotides of HCABA58X coding sequence. The 3' sequence 5' GACTGGATCCGAAGGTGTAGGCCCCTAC 3' (SEQ ID NO:4) contains complementary sequences to a BamHI site and is followed by 18 nucleotides of HCABA5X. The restriction enzyme sites correspond to the restriction enzyme sites on the bacterial expression vector pQE-70 (Qiagen, Inc. Chatsworth, Calif.). pQE-70 encodes antibiotic resistance (Ampr), a bacterial origin of replication (ori), an IPTG-regulatable promoter operator (P/O), a ribosome binding site (RBS), a 6-His tag ancL restriction enzyme sites. pQE-70 is then digested with SphI and BamHI. The amplified sequences are ligated into pQE-70 and are inserted in frame with the sequence encoding for the histidine tag and the RBS. The ligation mixture is then used to transform *E. coli* strain M15/rep5 (Qiagen, Inc.) by the procedure described in Sambrook, J. et al., Molecular Cloning: A Laboratory Manual, Cold Spring Laboratory Press, (1989). M15/rep5 contains multiple copies of the plasmid pREP4, which expresses the lacI repressor and also confers kanamycin resistance (Kan'). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized HCABA58X is purified from this solution by chromatography on a Nickel-Chelate column under conditions that allow for tight binding by proteins containing the 6-His tag (Hochuli, E. et al., J. Chromatography 411:177–184 (1984)). HCABA58X protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Cloning and Expression of HCABA58X Using the Baculovirus Expression System

The DNA sequence encoding the HCABA58X protein, ATCC # 97376, is amplified using PCR oligonucleotide primers corresponding to the 5' and 3' sequences of the gene.

The primer sequences are as follows: 5' GAGCGGATC-CGCCATC ATGCTCCCCTGCGCCTCCTG 3' (SEQ ID NO:5), has a BamHI restriction enzyme site (in bold) followed by 6 nucleotides resembling an efficient signal for the initiation of translation in eukaryotic cells (Kozak, M., J. Mol. Biol., 196:947–950 (1987) (the initiation codon for translation is "ATG"), followed by 20 nucleotides corresponding to the 5' end of the HCABA58X coding sequence.

The 3' primer 5' GACTGGTACCCTGCCCCTCACAA-CAGGCT (SEQ ID NO:6) contains the cleavage site for the restriction endonuclease Asn718 (bold) and 20 nucleotides complementary to the 3' end of the HCABA58X gene. The amplified sequences are isolated from a 1% agarose gel using a commercially available kit ("Geneclean," BIO 101 Inc., La Jolla, Calif.). The fragment is then digested with the endonucleases BamHI and Asp718 and then purified again on a 1% agarose gel. This fragment is designated F2.

The vector pA2 is used (modification of pVL941 vector, discussed below) for the expression of the HCABA58X protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases. The polyadenylation site of the simian virus (SV)40 is used for efficient polyadenylation. For an easy selection of recombinant virus the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used such as pAc373, pRG1, pVL941 and pAcIM1 (Luckow, V. A. and Summers, M. D., Virology, 170:31–39).

The plasmid is digested with the restriction enzymes BamHI and Asp718 and then dephosphorylated using calf intestinal phosphatase by procedures known in the art. The DNA is then isolated from a 1 agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. E.coli HB101 cells are then transformed and bacteria identified that contained the plasmid (pBacHCABA58X) with the HCABA58X gene using the restriction enzymes BamHI and Asp718. The sequence of the cloned fragment is confirmed by DNA sequencing.

5 μg of the plasmid pBacHCABA58X is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBacHCABA58X are mixed in a sterile well of a microtiter plate containing 50 μl of serum free Grace's medium (Life Technologies Inc., Gaithersburg, Md.). Afterwards 10 μl Lipofectin plus 90 Al Grace's medium are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the virus is added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-HCABA58X at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 3

Expression of Recombinant HCABA58X in COS Cells

The expression of plasmid, HCABA58X HA is derived from a vector pcDNA3/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire HCABA58X precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding HCABA58X, ATCC # 97376, is constructed by PCR using two primers: the 5' primer 5' GACT GGATCC GCC ACC ATG CTCCCCT-GCGCCTCCTG 3' (SEQ ID NO:7) contains a BamHI site (in bold) followed by 6 nucleotides resembling an efficient translation initiation sequence in eukaryotic cells and followed by 20 nucleotides of HCABA58X coding sequence starting from the initiation codon; the 31 sequence 5' GACT TCTAGA TTA AGC GTA GTC TGG GAC GTC GTA TGG GTA GTT CTC CTT CAT GTC CTT GAA GGT GTA GGC CCC TAC 3' (SEQ ID NO:8) contains complementary sequences to an HA tag seqeunce, the last 18 nucleotides of the HCABA58X domain and an XbaI site. Therefore, the PCR product contains a BamHI site, 1374 base pair coding sequence and an XbaI site. The PCR amplified DNA fragment and the vector, pcDNA3/Amp, are digested with BamHI and XbaI restriction enzyme and ligated. The ligation mixture is transformed into E. coli strain SURE (available from Stratagene Cloning Systems, La Jolla, Calif. 92037) the transformed culture is plated on ampicillin media plates and resistant colonies are selected. Plasmid DNA is isolated from transEormants and examined by restriction analysis for the presence of the correct fragment. For expression of the recombinant HCABA58X, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the HCABA58X HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

EXAMPLE 4

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and., therefore, within the scope of the appended claims, the invention may be practiced otherwise than as particularly described.

What is claimed is:

1. An isolated polynucleotide comprising a nucleic acid sequence selected from the group consisting of:
   (a) a nucleic acid sequence encoding the polypeptide set forth as amino acid residues 1 to 443 of SEQ ID NO:2;
   (b) a nucleic acid sequence encoding the polypeptide set forth as amino acid residues 2 to 443 of SEQ ID NO:2;
   (c) a nucleic acid sequence encoding at least 30 contiguous amino acid residues of SEQ ID NO:2; and
   (d) a nucleic acid sequence complementary to the nucleic acid sequence of (a), (b) or (c).

2. The isolated polynucleotide of claim 1 wherein the nucleic acid sequence is (a).

3. The isolated polynucleotide of claim 1 wherein the nucleic acid sequence is (b).

4. The isolated polynucleotide of claim 3 wherein the nucleic acid sequence is shown as nucleotides 197 to 1453 in SEQ ID NO:1.

5. The isolated polynucleotide of claim 4 wherein the nucleic acid sequence is shown as nucleotides 125 to 1453 in SEQ ID NO:1.

6. The isolated polynucleotide of claim 1 wherein the nucleic acid sequence is (c).

7. The isolated polynucleotide of claim 6 wherein the nucleic acid sequence encodes at least 50 contiguous amino acid residues of SEQ ID NO:2.

8. The isolated polynucleotide of claim 1 wherein said polynucleotide is DNA and further wherein said nucleic acid sequence is (a), (b) or (c).

9. A recombinant vector comprising the DNA of claim 8.

10. A recombinant host cell comprising the DNA of claim 8.

11. A process for producing a polypeptide comprising expressing from the host cell of claim 10 the encoded polypeptide and recovering said polypeptide.

12. A polynucleotide comprising the DNA of claim 8 linked to a heterologous regulatory sequence which controls gene expression.

13. The isolated polynucleotide of claim 1 consisting of a nucleic acid sequence selected from the group consisting of:
   (a) a nucleic acid sequence encoding the polypeptide set forth as amino acid residues 1 to 443 of SEQ ID NO:2;
   (b) a nucleic acid sequence encoding the polypeptide set forth as amino acid residues 2 to 443 of SEQ ID NO:2;
   (c) a nucleic acid sequence encoding at least 30 contiguous amino acid residues of SEQ ID NO:2; and
   (d) a nucleic acid sequence complementary to the nucleic acid sequence of (a), (b) or (c).

14. An isolated polynucleotide comprising the polynucleotide of claim 13 fused to a heterologous polynucleotide.

15. An isolated polynucleotide comprising a nucleic acid sequence selected from the group consisting of:

(a) a nucleic acid sequence encoding the polypeptide encoded by the human cDNA contained in ATCC Deposit No. 97376;
   (b) a nucleic acid sequence encoding the mature polypeptide encoded by the human cDNA contained in ATCC Deposit No. 97376;
   (c) a nucleic acid sequence encoding at least 30 contiguous amino acid residues of the polypeptide encoded by the human cDNA contained in ATCC Deposit No. 97376; and
   (d) a nucleic acid sequence complementary to the nucleic acid sequence of (a), (b) or (c).

16. The isolated polynucleotide of claim 15 wherein said nucleic acid sequence is (a).

17. The isolated polynucleotide of claim 15 wherein said nucleic acid sequence is (b).

18. The isolated polynucleotide of claim 15 wherein said nucleic acid sequence is (c).

19. The isolated polynucleotide of claim 18 wherein said nucleic acid sequence encodes at least 50 contiguous amino acid residues of the polypeptide encoded by the human cDNA contained in ATCC Deposit No. 97376.

20. The isolated polynucleotide of claim 15 wherein said polynucleotide is DNA and further wherein said nucleic acid sequence is (a), (b) or (c).

21. A recombinant vector comprising the DNA of claim 20.

22. A recombinant host cell comprising the DNA of claim 20.

23. A process for producing a polypeptide comprising expressing from the host cell of claim 22 the encoded polypeptide and recovering said polypeptide.

24. The isolated DNA of claim 20 linked to regulatory sequence which controls gene expression.

25. The isolated polynucleotide of claim 15 consisting of a nucleic acid sequence selected from the group consisting of:
   (a) a nucleic acid sequence encoding the polypeptide encoded by the human cDNA contained in ATCC Deposit No. 97376;
   (b) a nucleic acid sequence encoding the mature polypeptide encoded by the human cDNA contained in ATCC Deposit No. 97376;
   (c) a nucleic acid sequence encoding at least 30 contiguous amino acid residues of the polypeptide encoded by the human cDNA contained in ATCC Deposit No. 97376; and
   (d) a nucleic acid sequence complementary to the nucleic acid sequence of (a), (b) or (c).

26. An isolated polynucleotide comprising the polynucleotide of claim 25 fused to a heterologous polynucleotide.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1531 base pairs
      (B) TYPE: nucleic acid -continued

```
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 125..1453

(xi) SEQUENCE DESCRIPTION: SEQ ID NO:1:

GGAATTCGGC ACGAGCGTCC AGGGAGCTGT GCCGTCCGCC CGTCCGTCTG CCCGCAGGCA        60

TTGCCCGAGC CAGCCGAGCC GCCAGAGCCG CGGGCCGCGG GGGTGTCGCG GGCCCAACCC       120

CAGG ATG CTC CCC TGC GCC TCC TGC CTA CCC GGG TCT CTA CTG CTC TGG       169
     Met Leu Pro Cys Ala Ser Cys Leu Pro Gly Ser Leu Leu Leu Trp
      1               5                  10                  15

GCG CTG CTA CTG TTG CTC TTG GGA TCA GCT TCT CCT CAG GAT TCT GAA        217
Ala Leu Leu Leu Leu Leu Leu Gly Ser Ala Ser Pro Gln Asp Ser Glu
                 20                  25                  30

GAG CCC GAC AGC TAC ACG GAA TGC ACA GAT GGC TAT GAG TGG GAC CCA        265
Glu Pro Asp Ser Tyr Thr Glu Cys Thr Asp Gly Tyr Glu Trp Asp Pro
                 35                  40                  45

GAC AGC CAG CAC TGC CGG GAT GTC AAC GAG TGT CTG ACC ATC CCT GAG        313
Asp Ser Gln His Cys Arg Asp Val Asn Glu Cys Leu Thr Ile Pro Glu
             50                  55                  60

GCC TGC AAG GGG GAA ATG AAG TGC ATC AAC CAC TAC GGG GGC TAC TTG        361
Ala Cys Lys Gly Glu Met Lys Cys Ile Asn His Tyr Gly Gly Tyr Leu
         65                  70                  75

TGC CTG CCC CGC TCC GCT GCC GTC ATC AAC GAC CTA CAC GGC GAG GGA        409
Cys Leu Pro Arg Ser Ala Ala Val Ile Asn Asp Leu His Gly Glu Gly
 80                  85                  90                  95

CCC CCG CCA CCA GTG CCT CCC GCT CAA CAC CCC AAC CCC TGC CCA CCA        457
Pro Pro Pro Pro Val Pro Pro Ala Gln His Pro Asn Pro Cys Pro Pro
                100                 105                 110

GGC TAT GAG CCC GAC GAT CAG GAC AGC TGT GTG GAT GTG GAC GAG TGT        505
Gly Tyr Glu Pro Asp Asp Gln Asp Ser Cys Val Asp Val Asp Glu Cys
                115                 120                 125

GCC CAG GCC CTG CAC GAC TGT CGC CCC AGC CAG GAC TGC CAT AAC TTG        553
Ala Gln Ala Leu His Asp Cys Arg Pro Ser Gln Asp Cys His Asn Leu
            130                 135                 140

CCT GGC TCC TAT CAG TGC ACC TGC CCT GAT GGT TAC CGC AAG ATC GGG        601
Pro Gly Ser Tyr Gln Cys Thr Cys Pro Asp Gly Tyr Arg Lys Ile Gly
145                 150                 155

CCC GAG TGT GTG GAC ATA GAC GAG TGC CGC TAC CGC TAC TGC CAG CAC        649
Pro Glu Cys Val Asp Ile Asp Glu Cys Arg Tyr Arg Tyr Cys Gln His
160                 165                 170                 175

CGC TGC GTG AAC CTG CCT GGC TCC TTC CGC TGC CAG TGC GAG CCG GGC        697
Arg Cys Val Asn Leu Pro Gly Ser Phe Arg Cys Gln Cys Glu Pro Gly
                180                 185                 190

TTC CAG CTG GGG CCT AAC AAC CGC TCC TGT GTT GAT GTG AAC GAG TGT        745
Phe Gln Leu Gly Pro Asn Asn Arg Ser Cys Val Asp Val Asn Glu Cys
                195                 200                 205

GAC ATG GGG GCC CCA TGC GAG CAG CGC TGC TTC AAC TCC TAT GGG ACC        793
Asp Met Gly Ala Pro Cys Glu Gln Arg Cys Phe Asn Ser Tyr Gly Thr
            210                 215                 220

TTC CTG TGT CGC TGC CAC CAG GGC TAT GAG CTG CAT CGG GAT GGC TTC        841
Phe Leu Cys Arg Cys His Gln Gly Tyr Glu Leu His Arg Asp Gly Phe
            225                 230                 235

TCC TGC AGT GAT ATT GAT GAG TGT AGC TAC TCC AGC TAC CTC TGT CAG        889
Ser Cys Ser Asp Ile Asp Glu Cys Ser Tyr Ser Ser Tyr Leu Cys Gln
240                 245                 250                 255

TAC CGC TGC GTC AAC GAG CCA GGC CGT TTC TCC TGC CAC TGC CCA CAG        937
```

-continued

```
            Tyr Arg Cys Val Asn Glu Pro Gly Arg Phe Ser Cys His Cys Pro Gln
                        260                 265                 270

GGT TAC CAG CTG CTG GCC ACA CGC CTC TGC CAA GAC ATT GAT GAG TGT           985
Gly Tyr Gln Leu Leu Ala Thr Arg Leu Cys Gln Asp Ile Asp Glu Cys
            275                 280                 285

GAG TCT GGT GCG CAC CAG TGC TCC GAG GCC CAA ACC TGT GTC AAC TTC          1033
Glu Ser Gly Ala His Gln Cys Ser Glu Ala Gln Thr Cys Val Asn Phe
            290                 295                 300

CAT GGG GGC TAC CGC TGC GTG GAC ACC AAC CGC TGC GTG GAG CCC TAC          1081
His Gly Gly Tyr Arg Cys Val Asp Thr Asn Arg Cys Val Glu Pro Tyr
            305                 310                 315

ATC CAG GTC TCT GAG AAC CGC TGT CTC TGC CCG GCC TCC AAC CCT CTA          1129
Ile Gln Val Ser Glu Asn Arg Cys Leu Cys Pro Ala Ser Asn Pro Leu
320                 325                 330                 335

TGT CGA GAG CAG CCT TCA TCC ATT GTG CAC CGC TAC ATG ACC ATC ACC          1177
Cys Arg Glu Gln Pro Ser Ser Ile Val His Arg Tyr Met Thr Ile Thr
            340                 345                 350

TCG GAG CGG AGC GTG CCC GCT GAC GTG TTC CAG ATC CAG GCG ACC TCC          1225
Ser Glu Arg Ser Val Pro Ala Asp Val Phe Gln Ile Gln Ala Thr Ser
            355                 360                 365

GTC TAC CCC GGT GCC TAC AAT GCC TTT CAG ATC CGT GCT GGA AAC TCG          1273
Val Tyr Pro Gly Ala Tyr Asn Ala Phe Gln Ile Arg Ala Gly Asn Ser
            370                 375                 380

CAG GGG GAC TTT TAC ATT AGG CAA ATC AAC AAC GTC AGC GCC ATG CTG          1321
Gln Gly Asp Phe Tyr Ile Arg Gln Ile Asn Asn Val Ser Ala Met Leu
            385                 390                 395

GTC CTC GCC CGG CCG GTG ACG GGC CCC CGG GAG TAC GTG CTG GAC CTG          1369
Val Leu Ala Arg Pro Val Thr Gly Pro Arg Glu Tyr Val Leu Asp Leu
400                 405                 410                 415

GAG ATG GTC ACC ATG AAT TCC CTC ATG AGC TAC CGG GCC AGC TCT GTA          1417
Glu Met Val Thr Met Asn Ser Leu Met Ser Tyr Arg Ala Ser Ser Val
            420                 425                 430

CTG AGG CTC ACC GTC TTT GTA GGG GCC TAC ACC TTC TGAGGAGCAG               1463
Leu Arg Leu Thr Val Phe Val Gly Ala Tyr Thr Phe
            435                 440

GAGGGAGCCA CCCTCCCTGC AGCTACCCTA GCTGAGGAGC CTGTTGTGAG GGGCAGAATG        1523

AGAAAGGC                                                                 1531
```

(2) INFORMATION FOR SEQ ID NO:2:

(i) SEQUENCE CHARACTERISTICS:
      (A) LENGTH: 443 amino acids
      (B) TYPE: amino acid
      (D) TOPOLOGY: linear (ii) MOLECULE TYPE: protein (xi) SEQUENCE DESCRIPTION: SEQ ID NO:2:

```
Met Leu Pro Cys Ala Ser Cys Leu Pro Gly Ser Leu Leu Leu Trp Ala
 1                5                  10                  15

Leu Leu Leu Leu Leu Leu Gly Ser Ala Ser Pro Gln Asp Ser Glu Glu
                20                  25                  30

Pro Asp Ser Tyr Thr Glu Cys Thr Asp Gly Tyr Glu Trp Asp Pro Asp
            35                  40                  45

Ser Gln His Cys Arg Asp Val Asn Glu Cys Leu Thr Ile Pro Glu Ala
        50                  55                  60

Cys Lys Gly Glu Met Lys Cys Ile Asn His Tyr Gly Gly Tyr Leu Cys
65                  70                  75                  80

Leu Pro Arg Ser Ala Ala Val Ile Asn Asp Leu His Gly Glu Gly Pro
                85                  90                  95
```

```
Pro Pro Pro Val Pro Pro Ala Gln His Pro Asn Pro Cys Pro Pro Gly
            100                 105                 110

Tyr Glu Pro Asp Asp Gln Asp Ser Cys Val Asp Val Asp Glu Cys Ala
            115                 120                 125

Gln Ala Leu His Asp Cys Arg Pro Ser Gln Asp Cys His Asn Leu Pro
            130                 135                 140

Gly Ser Tyr Gln Cys Thr Cys Pro Asp Gly Tyr Arg Lys Ile Gly Pro
145                 150                 155                 160

Glu Cys Val Asp Ile Asp Glu Cys Arg Tyr Arg Tyr Cys Gln His Arg
                165                 170                 175

Cys Val Asn Leu Pro Gly Ser Phe Arg Cys Gln Cys Glu Pro Gly Phe
            180                 185                 190

Gln Leu Gly Pro Asn Asn Arg Ser Cys Val Asp Val Asn Glu Cys Asp
            195                 200                 205

Met Gly Ala Pro Cys Glu Gln Arg Cys Phe Asn Ser Tyr Gly Thr Phe
            210                 215                 220

Leu Cys Arg Cys His Gln Gly Tyr Glu Leu His Arg Asp Gly Phe Ser
225                 230                 235                 240

Cys Ser Asp Ile Asp Glu Cys Ser Tyr Ser Ser Tyr Leu Cys Gln Tyr
                245                 250                 255

Arg Cys Val Asn Glu Pro Gly Arg Phe Ser Cys His Cys Pro Gln Gly
            260                 265                 270

Tyr Gln Leu Leu Ala Thr Arg Leu Cys Gln Asp Ile Asp Glu Cys Glu
            275                 280                 285

Ser Gly Ala His Gln Cys Ser Glu Ala Gln Thr Cys Val Asn Phe His
            290                 295                 300

Gly Gly Tyr Arg Cys Val Asp Thr Asn Arg Cys Val Glu Pro Tyr Ile
305                 310                 315                 320

Gln Val Ser Glu Asn Arg Cys Leu Cys Pro Ala Ser Asn Pro Leu Cys
            325                 330                 335

Arg Glu Gln Pro Ser Ser Ile Val His Arg Tyr Met Thr Ile Thr Ser
            340                 345                 350

Glu Arg Ser Val Pro Ala Asp Val Phe Gln Ile Gln Ala Thr Ser Val
            355                 360                 365

Tyr Pro Gly Ala Tyr Asn Ala Phe Gln Ile Arg Ala Gly Asn Ser Gln
            370                 375                 380

Gly Asp Phe Tyr Ile Arg Gln Ile Asn Asn Val Ser Ala Met Leu Val
385                 390                 395                 400

Leu Ala Arg Pro Val Thr Gly Pro Arg Glu Tyr Val Leu Asp Leu Glu
            405                 410                 415

Met Val Thr Met Asn Ser Leu Met Ser Tyr Arg Ala Ser Ser Val Leu
            420                 425                 430

Arg Leu Thr Val Phe Val Gly Ala Tyr Thr Phe
            435                 440

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

```
GATCGCATGC TCCCCTGCGC CTCCTG                                                26
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GACTGGATCC GAAGGTGTAG GCCCCTAC                                              28
```

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GAGCGGATCC GCCATCATGC TCCCCTGCGC CTCCTG                                     36
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GACTGGTACC CTGCCCCTCA CAACAGGCTC                                            30
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GACTGGATCC GCCACCATGC TCCCCTGCGC CTCCTG                                     36
```

(2) INFORMATION FOR SEQ ID NO:8:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GACTTCTAGA TTAAGCGTAG TCTGGGACGT CGTATGGGTA GTTCTCCTTC ATGTCCTTGA           60
AGGTGTAGGC CCCTAC                                                           76
```

(2) INFORMATION FOR SEQ ID NO:9:

(i) SEQUENCE CHARACTERISTICS:
  (A) LENGTH: 387 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:9:

```
Met Ala Thr Ser Gly Val Leu Pro Gly Gly Phe Val Ala Ser Ala
1               5                   10                  15

Ala Ala Val Ala Gly Pro Glu Met Gln Thr Gly Arg Asn Asn Phe Val
            20                  25                  30

Ile Arg Arg Asn Pro Ala Asp Pro Gln Arg Ile Pro Ser Asn Pro Ser
        35                  40                  45

His Arg Ile Gln Cys Ala Ala Gly Tyr Glu Gln Ser Glu His Asn Val
    50                  55                  60

Cys Gln Asp Ile Asp Glu Cys Thr Ala Gly Thr His Asn Cys Arg Ala
65                  70                  75                  80

Asp Gln Val Cys Ile Asn Leu Arg Gly Ser Phe Ala Cys Gln Cys Pro
                85                  90                  95

Pro Gly Tyr Gln Lys Arg Gly Glu Gln Cys Val Asp Ile Asp Glu Cys
                100                 105                 110

Thr Ile Pro Pro Tyr Cys His Gln Arg Cys Val Asn Thr Pro Gly Ser
            115                 120                 125

Phe Tyr Cys Gln Cys Ser Pro Gly Phe Gln Leu Ala Ala Asn Asn Tyr
        130                 135                 140

Thr Cys Val Asp Ile Asn Glu Cys Asp Ala Ser Asn Gln Cys Ala Gln
145                 150                 155                 160

Gln Cys Tyr Asn Ile Leu Gly Ser Phe Ile Cys Gln Cys Asn Gln Gly
                165                 170                 175

Tyr Glu Leu Ser Ser Asp Arg Leu Asn Cys Glu Asp Ile Asp Glu Cys
                180                 185                 190

Arg Thr Ser Ser Tyr Leu Cys Gln Tyr Gln Cys Val Asn Glu Pro Gly
            195                 200                 205

Lys Phe Ser Cys Met Cys Pro Gln Gly Tyr Gln Val Val Arg Ser Arg
        210                 215                 220

Thr Cys Gln Asp Ile Asn Glu Cys Glu Thr Thr Asn Glu Cys Arg Glu
225                 230                 235                 240

Asp Glu Met Cys Trp Asn Tyr His Gly Gly Phe Arg Cys Tyr Pro Arg
                245                 250                 255

Asn Pro Cys Gln Asp Pro Tyr Ile Leu Thr Pro Glu Asn Arg Cys Val
                260                 265                 270

Cys Pro Val Ser Asn Ala Met Cys Arg Glu Leu Pro Gln Ser Ile Val
            275                 280                 285

Tyr Lys Tyr Met Ser Ile Arg Ser Asp Arg Ser Val Pro Ser Asp Ile
        290                 295                 300

Phe Gln Ile Gln Ala Thr Thr Ile Tyr Ala Asn Thr Ile Asn Thr Phe
305                 310                 315                 320

Arg Ile Lys Ser Gly Asn Glu Asn Gly Glu Phe Tyr Leu Arg Gln Thr
                325                 330                 335

Ser Pro Val Ser Ala Met Leu Val Leu Val Lys Ser Leu Ser Gly Pro
            340                 345                 350

Arg Glu His Ile Val Asp Leu Glu Met Leu Thr Val Ser Ser Ile Gly
        355                 360                 365
```

```
Thr Phe Arg Thr Ser Ser Val Leu Arg Leu Thr Ile Ile Val Gly Pro
    370                 375                 380
Phe Ser Phe
385
```